(12) United States Patent
McGuire, Jr. et al.

(10) Patent No.: US 8,498,694 B2
(45) Date of Patent: Jul. 30, 2013

(54) SUBCUTANEOUS ACCESS DEVICE AND RELATED METHODS

(75) Inventors: James E. McGuire, Jr., Westerville, OH (US); David Melancthon Callard, Palo Alto, CA (US)

(73) Assignee: entrotech, inc., Columbus, OH (US)

( * ) Notice: Subject to any disclaimer, the term of this patent is extended or adjusted under 35 U.S.C. 154(b) by 505 days.

(21) Appl. No.: 12/460,121

(22) Filed: Jul. 13, 2009

(65) Prior Publication Data

US 2011/0009751 A1    Jan. 13, 2011

(51) Int. Cl.
*A61B 6/00* (2006.01)
*A61B 5/00* (2006.01)

(52) U.S. Cl.
USPC .......................................... 600/476; 600/344

(58) Field of Classification Search
USPC .................. 600/344, 362, 473, 476; 250/330, 250/372
See application file for complete search history.

(56) References Cited

U.S. PATENT DOCUMENTS

| | | |
|---|---|---|
| 3,966,855 A | 6/1976 | Hollenberg et al. |
| 4,044,253 A | 8/1977 | Crane |
| 4,107,980 A | 8/1978 | Crane et al. |
| 4,255,478 A | 3/1981 | Crane |
| 4,425,676 A | 1/1984 | Crane |
| 4,457,174 A | 7/1984 | Bar-Cohen et al. |
| 4,661,369 A | 4/1987 | Crane |
| 4,817,622 A | 4/1989 | Pennypacker et al. |
| 5,258,872 A | 11/1993 | Johnson et al. |
| 5,519,208 A | 5/1996 | Esparza et al. |
| 5,531,481 A * | 7/1996 | Wiltshire .................... 281/44 |
| 5,698,343 A | 12/1997 | Sutherland et al. |
| 5,735,273 A | 4/1998 | Kurnik et al. |
| 5,989,409 A | 11/1999 | Kurnik et al. |
| 6,032,070 A | 2/2000 | Flock et al. |
| 6,230,046 B1 | 5/2001 | Crane et al. |
| 6,522,911 B1 | 2/2003 | Toida et al. |
| 6,556,858 B1 | 4/2003 | Zeman |
| 6,573,503 B1 | 6/2003 | Bawolek et al. |
| 6,766,187 B1 | 7/2004 | Black et al. |
| 6,805,961 B1 | 10/2004 | Watanabe et al. |

(Continued)

FOREIGN PATENT DOCUMENTS

| | | |
|---|---|---|
| WO | WO-2004/093672 | 11/2004 |
| WO | WO-2006/074415 | 7/2006 |
| WO | WO-2007/016048 | 2/2007 |

OTHER PUBLICATIONS

Dunn, Michael R., et al., "Utilization of Infrared Trans-Illumination as an Aid for Peripheral Arterial Access," *Academic Emergency Medicine*, 12(5), Supp. 1, pp. 34-35 (2005).

(Continued)

*Primary Examiner* — Michael Rozanski
(74) *Attorney, Agent, or Firm* — The Griffith Law Firm, AP.C.; Lisa M. Griffith (57) ABSTRACT

A subcutaneous access device of the invention comprises: a multi-layered structure capable of use in a medical imaging procedure; a light source for transillumination of a body portion of interest of a patient's body; and an attachment portion for attaching the device to the patient's body in a manner such that the body portion of interest is outwardly exposed on a side of the patient's body opposite the light source. The device facilitates hands-free transillumination of the body portion of interest. Kits for subcutaneous access comprise the subcutaneous access device and a light detector for detecting light emitted from the subcutaneous access device.

31 Claims, 9 Drawing Sheets

U.S. PATENT DOCUMENTS

| | | | |
|---|---|---|---|
| 6,855,743 | B1 | 2/2005 | Gvozdic |
| 6,862,542 | B2 | 3/2005 | Lockhart et al. |
| 6,889,075 | B2 | 5/2005 | Marchitto et al. |
| 6,923,762 | B1 | 8/2005 | Creaghan |
| 7,235,750 | B1 | 6/2007 | Coutu et al. |
| 7,239,909 | B2 | 7/2007 | Zeman |
| 7,532,746 | B2 | 5/2009 | Marcotte et al. |
| 2002/0016533 | A1 | 2/2002 | Marchitto et al. |
| 2003/0018271 | A1 | 1/2003 | Kimble |
| 2003/0069509 | A1 | 4/2003 | Matzinger et al. |
| 2004/0215081 | A1 | 10/2004 | Crane et al. |
| 2005/0168980 | A1 | 8/2005 | Dryden et al. |
| 2006/0122515 | A1 | 6/2006 | Zeman et al. |
| 2006/0173360 | A1 | 8/2006 | Kalafut et al. |
| 2007/0032721 | A1 | 2/2007 | Crane et al. |
| 2007/0276258 | A1 | 11/2007 | Crane |

OTHER PUBLICATIONS

"Infrared Imaging Systems 510(k) Application," (Sep. 28, 2004).

"Venoscope II Transilluminator—The Vein Finder: Instructions for Use," Venoscope, LLC P.O. Box 52703 Lafayette, LA 70505-2703.

"Natus Product Catalog" (2009).

"Veinlite—The Best Vein Finder For Vein Access In Children, Neonates, Emergency Medicine, Critical Care, Radiology And Oncology: Unsurpassed Imaging Of Varicose Veins Anywhere On The Body For Sclerotherapy And Finding Reticulars," www.veinlite.com, (Aug. 13, 2009).

Meltzer, Pete, "Vein Viewing Technology Provides Life Saving Imagery for Battlefield Wounded," http://www.irimagesys.com/Other/IRIS_AFRL_vein_viewer_discovery.pdf.

"VeinViewer by Luminetx: Seeing is Believing," http://www.luminetx.com/Portals/0/pdf/VVGS%20General%20%20Broch%20(D00144F).pdf, (2006).

Hadaway, Lynn, "The IRIS Vascular Viewer: A New Imaging Technology to Improve Peripheral Access Success," http://www.genteramed.com/pdf/hadaway.pdf (May 16, 2005).

Mayo Clinic Staff, "Blood Donation: What to Expect," http://www.mayoclinic.com/health/blood-donation/MY00526/DSECTION=what-you-can-expect (May 27, 2009).

\* cited by examiner

SUBCUTANEOUS ACCESS DEVICE AND RELATED METHODS

BACKGROUND OF THE INVENTION

Many methods and apparatus for accessing subcutaneous structures (e.g., vessels, such as veins and arteries, or other structures) are known. One common need for subcutaneous access involves intravenous insertion or extraction of fluids, medications, or the like when administering medical treatment to a patient. Subcutaneous access may be needed in, for example, the following medical facilities and departments: emergency, labor and delivery, laboratory, oncology, operating room, intensive care unit, pediatrics, and pediatric and neonatal intensive care unit.

For example, in emergencies, every second counts, and finding a vein in a critically injured or ill patient can be highly difficult and time-consuming when delivery of medications, fluids, and/or nutrients is most critical. In labor and delivery, an intravenous access device is often immediately placed in a patient during the admitting process for hydration or to introduce medication. Pregnant women may have, for example, pregnancy-induced hypertension, vaso-constricted veins, and/or edema—all of which contribute to challenging venipuncture. There are many reasons that lab work is needed during the course of one's life, at times with varying states of health that can greatly affect the ease of accessing a patient's subcutaneous structures. In oncology, frequent infusion therapies often make a patient's peripheral vasculature fragile and limited. In the operating room, unsuccessful attempts at peripheral intravenous access delay many operations. In the intensive care unit, there are many factors that can change a critical patient's status in an instant. When peripheral access cannot be attained and a central venous catheter must be placed, a patient's risk for infection—particularly risky bacterial staph infections—goes up significantly. In pediatrics, children pose a particular challenge for venipuncture due to their relatively small vessels and limited access points. Often adding to these challenges are the fears of the child and the great anxiety of their parents. When the patient is in the highly sensitive pediatric and neonatal intensive care unit, the situation can be even more challenging.

In the administration of medical care to a patient requiring subcutaneous access, especially in an emergency situation, such as that encountered by a physician, nurse, emergency medical technician (EMT), or other health care provider, or in the treatment of an accident victim at the scene of the accident, or in the treatment of wounded on a battlefield by a medic, environmental conditions under which medical care is administered may be adverse. These conditions include those associated with nighttime lighting conditions. It is well settled that expeditious administration of medical care to a victim improves the prospects of the victim's recovery. For example, the life of a soldier wounded on the battlefield may depend on the immediate intravenous administration of blood plasma, other lost body fluids, or medications. Similar immediate procedures by a health care provider may be required in order to treat a victim at the scene of an accident. Further, during transport of a victim to a hospital or similar medical care facility, administration of medical procedures may be necessary, but difficult to perform, under poor lighting conditions or under other adverse conditions (e.g., those associated with torn clothing, bleeding, or other circumstances). Shock may have caused veins of a victim to partially collapse, or the patient may have veins that are difficult to find (such as in the treatment of infants or obese persons), which further complicates procedures for accessing the veins.

Having subcutaneous fluid extracted (e.g., having blood drawn) or starting an intravenous access can be an uncomfortable, or even painful, experience for patients. In addition to a fear of needles, many patients must unfortunately endure multiple needle sticks when a nurse or technician cannot easily find an appropriate access point. Not surprisingly, even with adequate environmental conditions, finding a subcutaneous structure such as a vein is not always an easy task. Even the most seasoned health care providers may have to stick a patient multiple times before successfully locating a vein. A number of factors can make it difficult to find a patient's veins, including: age, frequent (or lengthy) infusion therapies, multiple disease states, dehydration, hypertension, size and fragility of blood vessels, skin tone, and presence of edema or fatty tissue. Thus, ways to facilitate ease and comfort of subcutaneous access are desirable.

U.S. Pat. No. 6,230,046 describes a system and method for enhancing the visualization of veins, arteries, or other subcutaneous natural or foreign structures in the body and for facilitating intravenous insertion or extraction of fluids, medications, or the like in the administration of medical treatment to a patient. The system and method include a light source of selected wavelength(s) for illuminating or trans-illuminating a selected portion of the body and a low-level light detector and suitable filters for generating an image of the illuminated body portion.

See also U.S. Patent Publication No. 2004/0215081. Illustrated therein is an apparatus and method for image extravasation or infiltration in a forearm. The forearm is placed proximate a near infrared light source, between the light source and a detector.

Still further, U.S. Patent Publication No. 2007/0032721 describes a disposable light source patch for enhanced visualization of subcutaneous structures. The patches therein are stated to be adhesively attached to a body portion of a patient and suitable for use in conjunction with certain systems and methods, such as those described in U.S. Pat. No. 6,230,046.

Luminetx Corporation (Memphis, Tenn.) markets a product for location of subcutaneous veins and projection of real-time images of their location onto the surface of the skin. The product is commercially available under the VEINVIEWER trade designation.

Despite advances in imaging, especially for visualization of subcutaneous structures in a patient's body, current systems tend to be cumbersome and inefficient. For example, in known procedures for visualization of subcutaneous structures, proper support of a light source in order to accurately direct the light onto a body portion of interest may be an awkward procedure for the health care provider when treating a patient. Moreover, current devices distinctly comprise light source(s) and support structure(s) that are essentially separate components that may be used together but are not intrinsically combined as an optimized device and as such have significant light losses and inefficiencies. There is, therefore, a continued need for improved devices for imaging processes associated with subcutaneous access. Further, there is a need for subcutaneous access devices that are portable and capable of efficient use in a variety of environments.

BRIEF SUMMARY OF THE INVENTION

The present invention relates generally to medical devices and procedures, and more particularly to a subcutaneous access device useful for enhancing visualization of veins, arteries, and other subcutaneous structures of the body in the administration of medical treatment to a patient. Advantageously, apparatus of the invention are portable and capable of efficient use in a variety of environments.

A subcutaneous access device of the invention comprises: a multi-layered structure capable of use in a medical imaging procedure; a light source for transillumination of a body portion of interest of a patient's body; and an attachment portion for attaching the device to the patient's body in a manner such that the body portion of interest is outwardly exposed on a side of the patient's body opposite the light source. The device facilitates hands-free transillumination of the body portion of interest. Kits for subcutaneous access comprise the subcutaneous access device and a light detector for detecting light emitted from the subcutaneous access device.

DETAILED DESCRIPTION OF THE INVENTION

Subcutaneous access devices and methods of the invention facilitate rapid and convenient visualization of and easy and comfortable access to veins, arteries, and other subcutaneous structures within a patient's body. In contrast to conventional methods and apparatus for subcutaneous access, devices of the invention are advantageously portable and capable of efficient use in a variety of environments. Devices of the invention are capable of being simply and efficiently used when providing both routine and critical care in the administration of medical treatment to a patient. In exemplary embodiments, devices and methods of the invention are capably used in the field (e.g., proximate a battlefield) or in temporary battlefield installations (e.g., forward surgical units).

Devices of the invention are particularly useful in conjunction with and are an improvement to systems and methods described in U.S. Pat. No. 6,230,046 and U.S. Patent Publication No. 2007/0032721. According to the invention, a subcutaneous access device comprises at least a multi-layered structure capable of use in a medical imaging procedure where a portion of a patient's body is transilluminated. Although preferably integral to the subcutaneous access device in many embodiments, a light source is also necessary for the transillumination and is provided as a separate component when not integrated in the subcutaneous access device. The device is configured with a suitable attachment portion such that it can be rapidly and easily attached to a patient's body for hands-free transilluminance of a body portion of interest, preferably with low light loss. As such, devices of the invention are preferably attachable to a patient's body in a manner such that the body portion of interest is between a light source necessary when using the subcutaneous access device and a corresponding light detector, all together forming a kit for subcutaneous access.

In order to securely attach the subcutaneous access device to a patient's body for hands-free transilluminance of a body portion of interest, the device comprises a multi-layered structure capable of use in a medical imaging procedure. Any suitable multi-layered structure can be used for that purpose within subcutaneous access devices of the invention. One such multi-layered structure is a patch described in U.S. Patent Publication No. 2007/0032721.

In an exemplary embodiment, a subcutaneous access device of the invention comprises a multi-layered structure for supporting the light source and directing light to the body portion of interest. According to one aspect of this embodiment, the multi-layered structure comprises: an optically transparent layer for interfacing and optically coupling the light source with a body's surface and conforming to the surface topography of the body portion of interest, a support for the light source, and a reflective layer between the light source and optically transparent layer for redirecting light reflected from the body's surface, or scattered by the subcutaneous structures, back through the optically transparent layer into the body portion of interest under examination. In an alternative embodiment, the multi-layered structure comprises: an optically transparent layer for interfacing and optically coupling the light source with a body's surface and conforming to the surface topography of the body portion of interest, a support for the light source, and an absorbing layer between the light source and optically transparent layer for absorbing light reflected from the body's surface, or scattered by the subcutaneous structures, in order to provide improved imagery associated with the body portion of interest under examination.

According to a further embodiment, outwardly exposed edges of the multi-layered structure comprise a reflective material (e.g., aluminum foil or a similar metallic film) or an absorbing material (e.g., a carbon substrate or other suitable substrate material made from, coated with, and/or impregnated with a light absorbing dye), which may be laminated to a supporting structure (e.g., polyethylene terephthalate or laminates thereof) for further redirecting light in relation to the body portion of interest under examination. When outwardly exposed edges of the multi-layered structure comprise a reflective material, light is preferably redirected toward the body portion of interest. However, in some cases where light is scattered outward from the body point of interest to exposed edges of the multi-layered structure, the degree of light scattering may be so great that redirection of light back to the body point of interest may not improve imagery, but rather increase diffusion of imagery associated with the body portion of interest. In those cases, it is preferred that outwardly exposed edges of the multi-layered structure comprise an absorbing material. When the outwardly exposed edges of the multi-layered structure are configured as such, enhanced illumination of subcutaneous structures is facilitated.

In one embodiment, the multi-layered structure is disposable and is, or could be, efficiently replaced in its entirety between uses of the subcutaneous access device as desired or needed. In another embodiment, the multi-layered structure is capable of multiple effective uses, without the need for replacement of components thereof between multiple uses.

Figure 1:
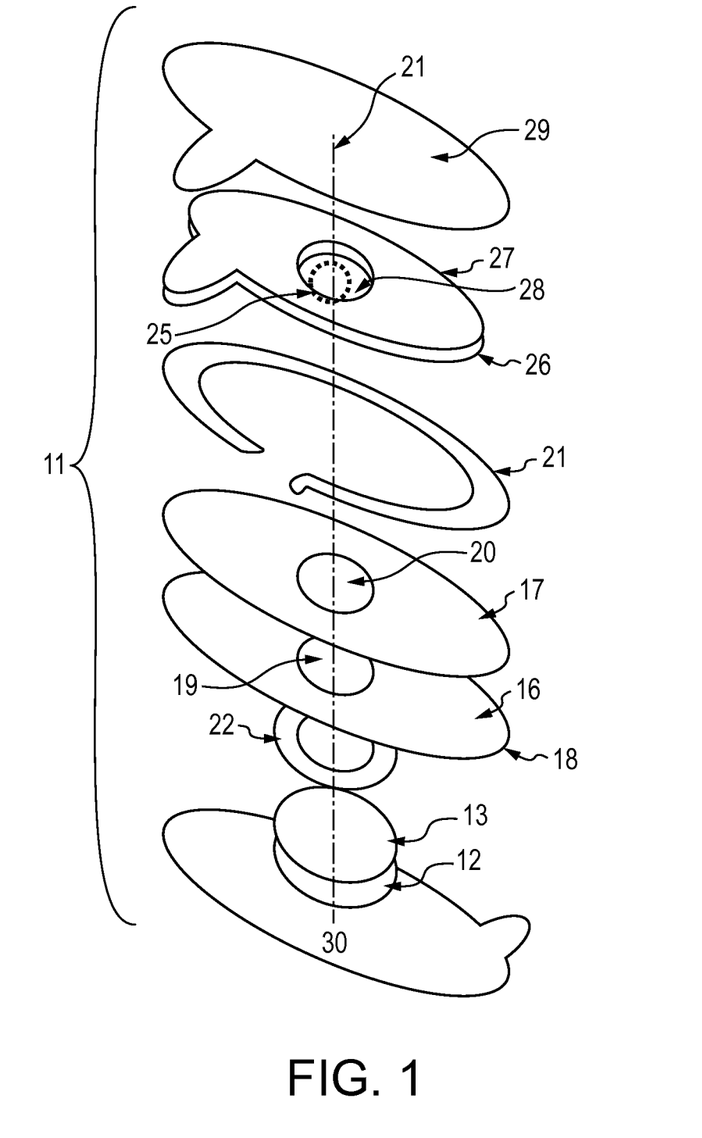
FIG. 1 is an at least partially exploded view of an exemplary multi-layered structure for use in subcutaneous access devices and methods of the present invention.

Referring now to FIG. 1, shown therein in an at least partially exploded view is an exemplary multi-layered structure 11, along with supporting structural elements, for use within a subcutaneous access device of the invention. The multi-layered structure 11 is configured to facilitate transillumination of a body portion of interest for visualization of subcutaneous structures therein.

Within the multi-layered structure 11, a first substantially optically transparent layer 12 is configured to interface with a surface of the body portion of interest to be illuminated. The terms "optical" or "optically" shall, in accordance with customary usage, be understood to include the ultraviolet, visible, near infrared, and infrared regions of the electromagnetic spectrum—having a wavelength of about 0.1 micron to about 1,500 microns.

In order to minimize reflections at the interface of the multi-layered structure 11 with a patient's body and to efficiently illuminate the body portion of interest with available light from a suitable light source 25 (illustrated by dashed lines in FIG. 1 and generally described further below) used in conjunction with the multi-layered structure 11, the refractive index of the optically transparent layer 12 should be closely matched to the refractive index of the body portion of interest. The refractive index of skin and other tissue of the body exposed to infrared light is generally about 1.3 to about 1.6. Accordingly, in an exemplary embodiment, the refractive index of the optically transparent layer 12 is about 1.33 to about 1.55.

Further, in order to efficiently couple light onto the body portion of interest, the optically transparent layer 12 preferably makes substantially intimate laminar contact with the body's surface in order to conform to various complex surface features of the skin. Such complex surface features include, for example, moles, hair, or various other skin conditions such as acne, psoriasis, lesions, or blemishes that would often result in pockets or gaps of air at the interface between the surface feature and the optically transparent layer 12. Such pockets or gaps of air would otherwise be likely to inhibit optical coupling with the body's surface and result in Fresnel reflections at such an interface. In addition to optical coupling, the optically transparent layer 12 also preferably provides a layer of thermal insulation between the light source 25 and the body's surface (i.e., acting as a thermal diffuser) so as to prevent discomfort to the patient or thermal damage to the skin and to provide a sterile barrier between the light source 25 and body surface should the multi-layered structure 11 or the light source 25 need to be placed near or across a wound.

Materials comprising the optically transparent layer 12 and useful in the multi-layered structure 11 include, for example, polyurethane, polyethylene, poly(meth)acrylate, polyester, polydimethylsiloxane, and hydrocolloid gels (also referred to as hydrogels) or other highly transmissive, conformable materials as known to those of ordinary skill in the art. Preferably, the optically transparent layer 12 comprises a hydrogel. Any suitable hydrogel can be used, preferably one that provides good optical coupling and thermal properties. An exemplary hydrogel material is available from entrotech, inc. (Columbus, Ohio) under the trade designation, entrotape 974.

The optically transparent layer 12 can be any suitable thickness. In an exemplary embodiment, the optically transparent layer 12 comprises a hydrogel layer having a thickness of about 500 microns to about 2,000 microns, preferably a thickness of about 800 microns to about 1,300 microns.

The multi-layered structure 11, as illustrated in FIG. 1, may also optionally comprise a support layer 13 adjacent the optically transparent layer 12 for enhanced prevention of the optically transparent layer 12 from tearing during use of the multi-layered structure 11. Materials comprising the support layer 13 and useful in the multi-layered structure 11 include, for example, polyethylene, polyurethane, or other suitable elastomeric materials, such as polydimethylsiloxane. In an exemplary embodiment, the support layer 13 comprises an infrared transparent polymer having a suitable refractive index of about 1.35 to about 1.5.

Structural support for the optically transparent layer 12 is also provided, for example, by first structural support layer 16 and second structural support layer 17, as illustrated in FIG. 1. The first and second structural support layers 16, 17 also help prevent the premature fracture or tearing of reflective or absorbing film 18, described below, in order to prevent leakage of light from the optically transparent layer 12 back through the first and second structural support layers 16, 17. Additionally, the first and second structural support layers 16, 17 provide some structural rigidity to the overall structure of the multi-layered structure 11 while permitting the optically transparent layer 12 to conform to the body's surface contour.

Each of the first and second structural support layers 16, 17 comprises any suitable structural material. For example, polyethylene, polyurethane, polyethylene terephthalate, and other structural polymers can be suitably used for the first and second structural support layers 16, 17.

Each of the first structural support layer 16 and the second structural support layer 17 also comprises a respective first and second central opening 19, 20 for passing of light through the multi-layered structure 11 proximate central axis 21 during use of the subcutaneous access device in order to illuminate a body's surface through the optically transparent layer 12. Each of the first central opening 19 and the second central opening 20 has any suitable shape and dimensions for desired passage of light through the multi-layered structure 11. Shape and/or dimensions of the first and second central openings 19, 20 can be the same or different, preferably each is approximately the same. In one embodiment, each of the first and second central openings 19, 20 has a diameter no greater than about 80% of the width of the respective first and second structural support layer 16, 17. In an exemplary embodiment, diameter of each of the first and second central openings 19, 20 is about 25 mm.

The first structural support layer 16 and the second structural support layer 17 can be any suitable thickness, both of which can be the same or different. In one embodiment, the first structural support layer 16 has a thickness of about 2 microns to about 30 microns and the second structural support layer 17 has a thickness of about 10 microns to about 55 microns.

As referenced in FIG. 1, a reflective or absorbing film 18 can optionally be included in the multi-layered structure 11 in order to direct light back through the optically transparent layer 12 or to absorb significantly scattered light, which light might be reflected or scattered from the body portion of interest at its interface with the body's surface or from the subcutaneous structures being observed. In the embodiment illustrated, the reflective or absorbing film 18 is supported on the underside of the first structural support layer 16 for directing, back through the optically transparent layer 12, or absorbing light that is backscattered from its interface with the body's surface. The reflective or absorbing film 18 also serves as a conductor of heat away from the light source 25.

The reflective or absorbing film 18 comprises any suitable light reflective or light absorbing material. An exemplary reflective material comprises aluminum. An exemplary absorbing material comprises a carbon substrate or other suitable substrate material made from, coated with, and/or impregnated with a light absorbing dye. The reflective or absorbing film 18 comprises any suitable thickness. Preferably, thickness of the reflective or absorbing film 18 is such that it facilitates conformability with the body portion of interest with which it interfaces during use of the subcutaneous access device. In one embodiment, the reflective or absorbing film 18 has a thickness of about 50 microns or less. An exemplary reflective film 18 comprises a 25-μm thick layer of aluminum foil.

In an exemplary embodiment, a structural support ring 22 provides adhesion between the support layer 13 supporting the optically transparent layer 12 and the reflective or absorbing film 18. Structural support ring 22 facilitates removal of layers 29 and 30 (described below) without wrinkling other layers of the multi-layered structure 11, thereby providing structural support for the multi-layered structure 11 after layers 29, 30 are removed when the multi-layered structure 11 is used as intended.

The structural support ring 22 comprises any suitable material, such as a synthetic polymeric or natural material. In one embodiment, the structural support ring 22 is formed from entrofilm 892, available from entrotech, inc. (Columbus, Ohio). The structural support ring 22 also comprises any suitable thickness. In an exemplary embodiment, the structural support ring 22 is about 50 microns to about 150 microns thick.

A light source 25 (illustrated by dashed lines in FIG. 1) may be inserted into and supported within first and second rings 26, 27 of the multi-layered structure 11. The first ring 26 optimally provides primary support for the light source 25. The second ring 27 prevents the first ring 26 from sticking to the light source 25 and facilitates release of the light source 25, if desired, when use of the multi-layered structure 11 is complete. As such, the second ring 27 optimally has a specific adhesion and thermal capability. Adhesion values of about 3.5 N/cm (2 pounds/linear inch) to about 17.5 N/cm (10 pounds/linear inch), preferably about 7.0 N/cm (4 pounds/linear inch) to about 10.5 N/cm (6 pounds/linear inch), as measurable using the ASTM D1000 90° peel adhesion test method were found to provide suitable adhesion for the second ring 27 consistent with purposes of the invention.

Extending through the first ring 26 and the second ring 27 is a central opening 28 for passing of light therethrough proximate central axis 21 during use of the subcutaneous access device. Similar to the first and second central openings 19, 20, the central opening 28 passing through the first and second rings 26, 27 has any suitable shape and dimensions for desired passage of light through the multi-layered structure 11. Shape and/or dimensions of the central opening 28 as it passes through each of the first and second rings 26, 27 can be the same or different, preferably approximately the same. In one embodiment, the central opening 28 has a diameter no greater than about 80% of the width of that of the first and second rings 26, 27. In an exemplary embodiment, diameter of the central opening 28 is about 25 mm.

The first ring 26 and the second ring 27 comprise any suitable material, preferably a conformable material such as foam or a foam-like material, which may be the same or different. An exemplary foam material comprises polyethylene foam. In a further embodiment, the first ring 26 comprises carbon-filled polyethylene foam, which aids in prevention of light leakage from the light source 25.

The first ring 26 and the second ring 27 comprise any suitable thickness, each of which may be the same or different. In one embodiment, the first ring 26 has a thickness of about 500 microns to about 2,100 microns. In one embodiment, the second ring 27 has a thickness of about 10 microns to about 100 microns.

In the embodiment illustrated in FIG. 1, a first protective pull-tab 29 comprising a protective contaminant barrier layer having a thickness of about 25 microns to about 130 microns, preferably about 50 microns to about 100 microns, is generally removed and discarded prior to attachment of the subcutaneous access device to the light source 25. A second protective pull-tab 30 comprising a protective contaminant barrier layer having a thickness of about 25 microns to about 180 microns, preferably about 50 microns to about 100 microns, is removed and discarded prior to attachment of the subcutaneous access device to the skin of a patient. The first and the second protective pull-tabs 29, 30 comprise any suitable material. An exemplary material comprises polyester.

Subcutaneous access devices of the invention are used in conjunction with a light source (such as the light source 25 in FIG. 1), which may be an integral light source, for illumination of the body portion of interest. The light source illuminates a body portion of interest with light of a selected wavelength. Any suitable light source can be used. Exemplary light sources include those emitting light in the ultraviolet, visible, near infrared, and infrared regions of the electromagnetic spectrum—i.e., light having a wavelength of about 0.1 micron to about 1,500 microns.

The light source is coupled to, or integrally includes, a corresponding power source enabling its use. The power source can be, and is preferably, integral to the subcutaneous access device or it can be a separate component used in conjunction with other components forming a kit for subcutaneous access.

In an exemplary embodiment, the light source operates via a portable power source, such as in the case of a battery-powered light emitting diode or chemiluminescent source, which is integral with the subcutaneous access device. Use of a portable power source further facilitates efficient use of the subcutaneous access device in, for example, the battlefield or in emergency situations. In one embodiment, a battery used for the portable power source comprises a rechargeable battery (e.g., those types of batteries used in cellular phones or portable music players, such as those sold by Apple, Inc. under the "iPod" trade designation). In an alternative embodiment, a battery used for the portable power source comprises a non-rechargeable battery. For example, such lithium batteries are sold by Tadiran (Port Washington, N.Y.) under the TLM-1530 trade designation.

In order to maximize simplicity and efficiency of use, subcutaneous access devices of the invention preferably comprise all electric components necessary for use of the device. In an exemplary embodiment, a subcutaneous access device of the invention comprises one or more integrated semiconductor chips capable of being programmed to control the light source. In a further embodiment, the one or more integrated semiconductor chips are capable of controlling a near-infrared light emitting diode (LED) light source of the device, including pulsation of the light source in synchronization with sensor gating when desired and/or measuring and indicating the usable power level within or applied to the device. Other components, such as communication mechanisms providing integrated control of device components are also preferably included within subcutaneous access devices of the invention.

Again, the device is configured with a suitable attachment portion (i.e., fastener) such that it can be rapidly and easily attached to a patient's body for hands-free transilluminance of a body portion of interest. The attachment portion preferably facilitates attachment of the device to a patient's body in a manner such that the body portion of interest is between the light source and a corresponding light detector.

Any suitable attachment mechanism can be employed for the attachment portion. In order to facilitate stable and repetitive attachment of the subcutaneous access device to a patient for hands-free transillumination of a body portion of interest, the attachment portion of the device is preferably resistant to accumulation of grime that can impair such attachment. As such, a non-adhesive attachment mechanism is preferred.

In one embodiment, a subcutaneous access device of the invention comprises an attachment portion for mechanical attachment of the device to a patient's arm. In an exemplary embodiment thereof, the subcutaneous access device comprises a watch configuration with a suitable attachment portion. Examples of suitable attachment portions include those comprising buckles, hook-and-loop fasteners (e.g., such as that available under the VELCRO trade designation, a registered trademark of Velcro Industries B.V. LLC of the Netherlands), laces, strings, bands (e.g., rubber bands), and similar mechanisms.

In another exemplary embodiment, the attachment portion of the device comprises an elastic sleeve or cuff, which may be inflatable, having a sufficiently smaller diameter than a limb to which the device is to be applied. According to this embodiment, when the subcutaneous access device is applied to the limb, the sleeve or cuff provides compression around the limb, securing the subcutaneous access device in place and holding the light source in close proximity to the body point of interest.

Figure 2A:
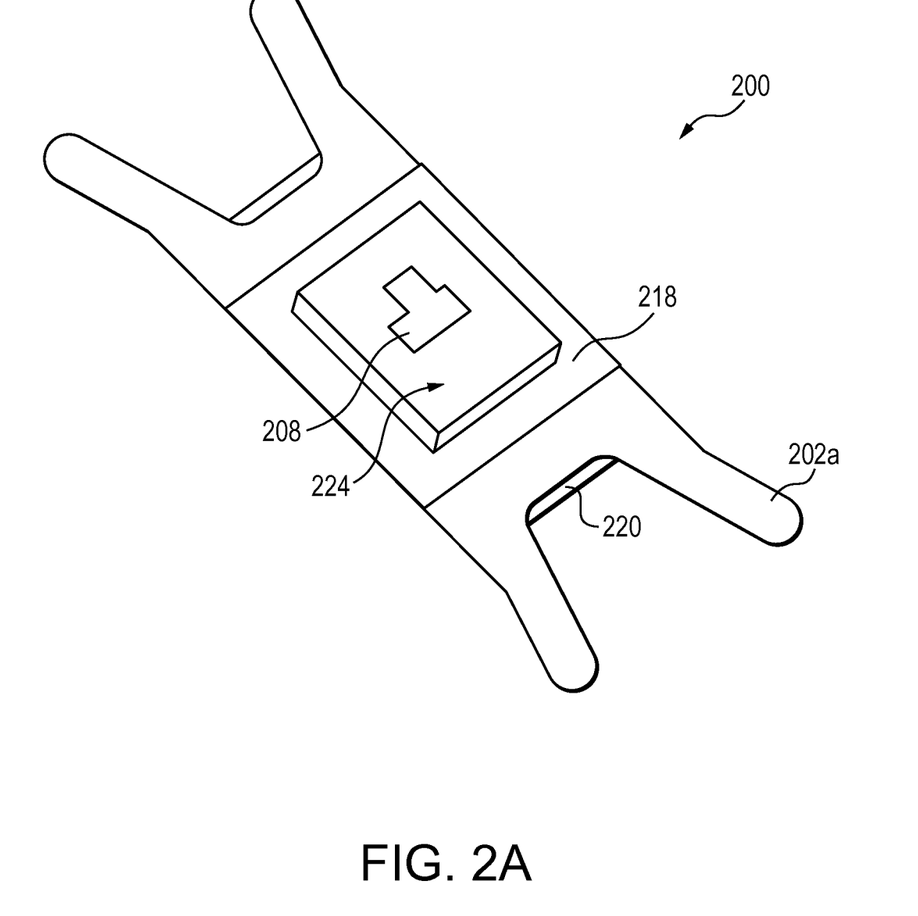
FIG. 2A is perspective view of an exemplary subcutaneous access device of the present invention, as viewed from a side opposite that from which light is transmitted.
Figure 2B:
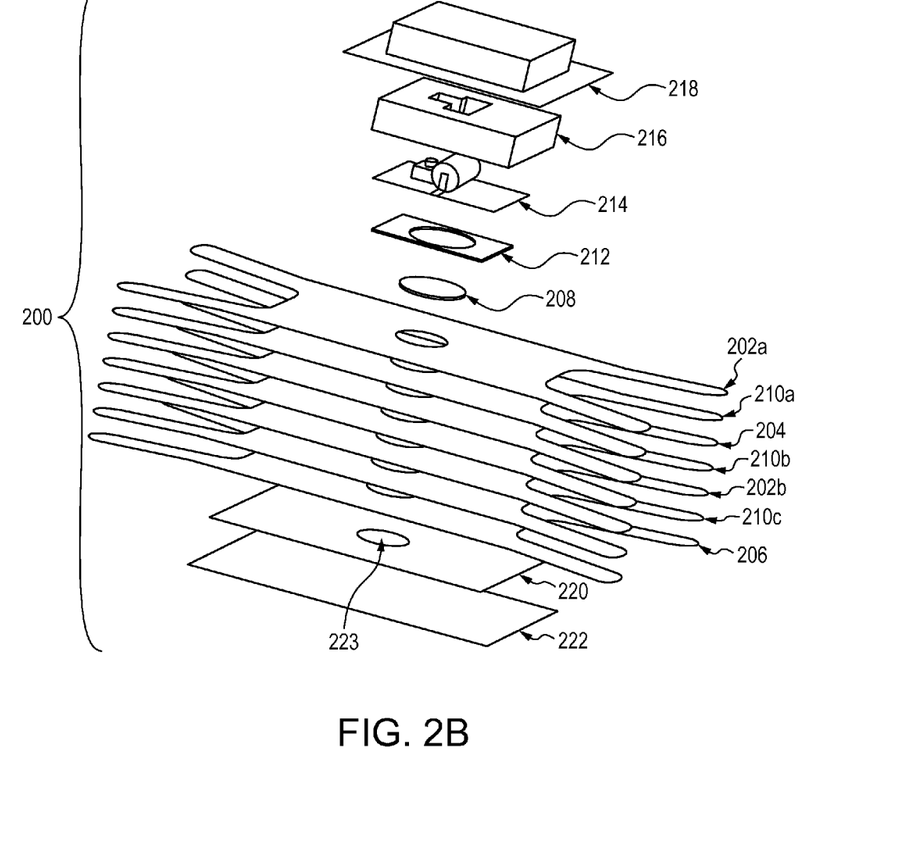
FIG. 2B is an at least partially exploded view of the subcutaneous access device illustrated in FIG. 2A.
Figure 2C:
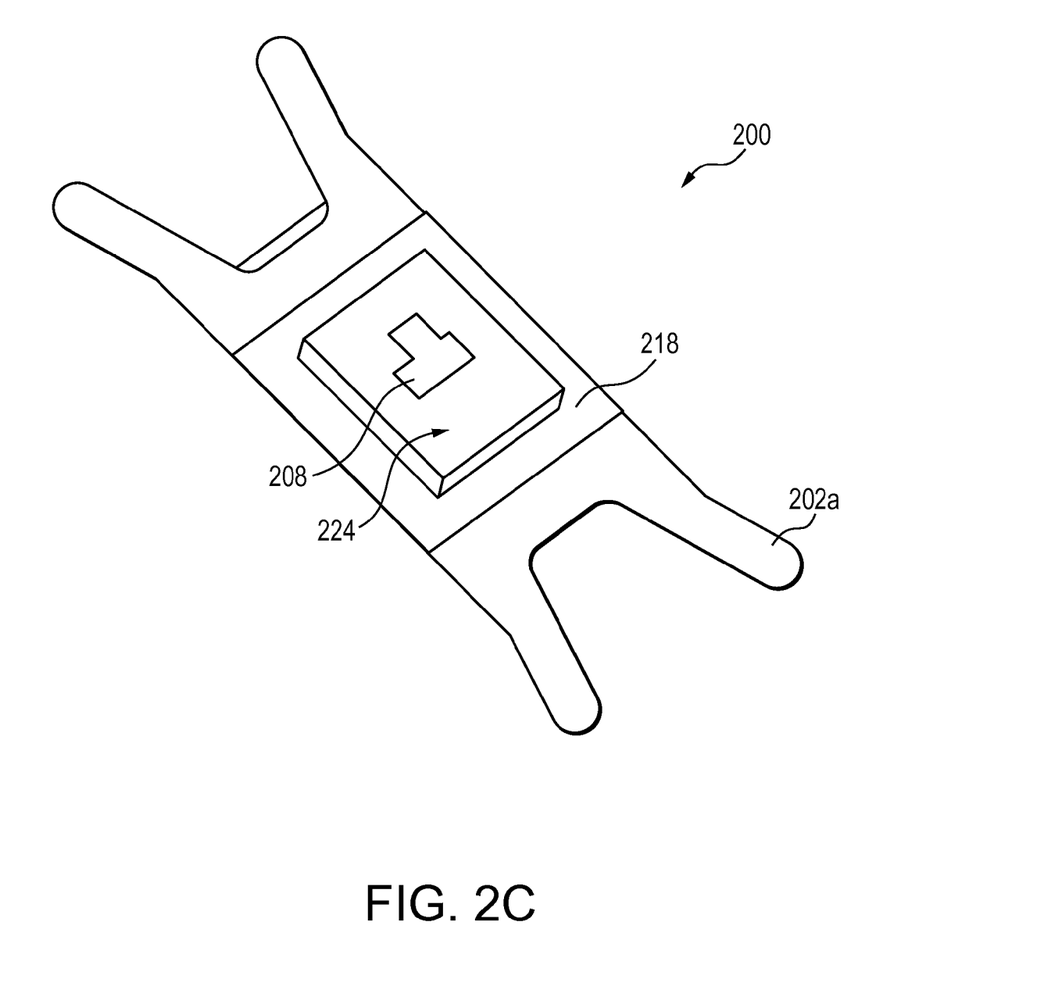
FIG. 2C is perspective view of an alternative embodiment of the exemplary subcutaneous access device illustrated in FIG. 2A, as viewed from a side opposite that from which light is transmitted.

Illustrated in FIG. 2A, as viewed from a side opposite that from which light is transmitted and with further details shown in the at least partially exploded view thereof illustrated in FIG. 2B, is an exemplary subcutaneous access device 200 adapted for attachment to a patient's arm. FIG. 2C is perspective view of an alternative embodiment of the exemplary subcutaneous access device illustrated in FIG. 2A, as also viewed from a side opposite that from which light is transmitted. Further details of the subcutaneous access device of FIG. 2C are shown in the at least partially exploded view thereof illustrated in FIG. 2D.

Laterally extending from the subcutaneous access device 200 is at least one layer of material capable of being securely attached at opposite ends thereof (i.e., at an attachment portion of the subcutaneous access device 200) around a patient's arm—i.e., a first and second securement layer 202a, 202b. The first and second securement layers 202a, 202b comprise not only structural support for the subcutaneous access device 200, but also facilitate secure mechanical attachment of the device 200 to a patient's arm.

Any suitable material and thickness thereof can be used for each of the first and second securement layers 202a, 202b, with the understanding that each of the first and second securement layers 202a, 202b may consist of a different material and/or a different thickness. Exemplary materials for the first and second securement layers 202a, 202b include polyethylene, polyurethane, polyethylene terephthalate, and other structural polymers. In one embodiment, the first securement layer 202a and the second securement layer 202b each comprise a 12.5-µm thick layer of black polyethylene terephthalate. Black or other dark colors are preferred for use in the first and second securement layers 202a and 202b so as to minimize the risk that the subcutaneous access device 200 is undesirably detected when used in low-light conditions, such as on battlefields.

It is also to be understand that, depending on the type of fastener, each of the first and second securement layers 202a, 202b may include additional layers of material (e.g., in the case of hook-and-loop fasteners, matable layers of material in the attachment portion of the subcutaneous access device 200 at opposite ends of the first and second securement layers 202a, 202b) and/or additional features (e.g., in the case of a subcutaneous access device 200 having an attachment portion comprising a buckle, a clasp).

Figure 2D:
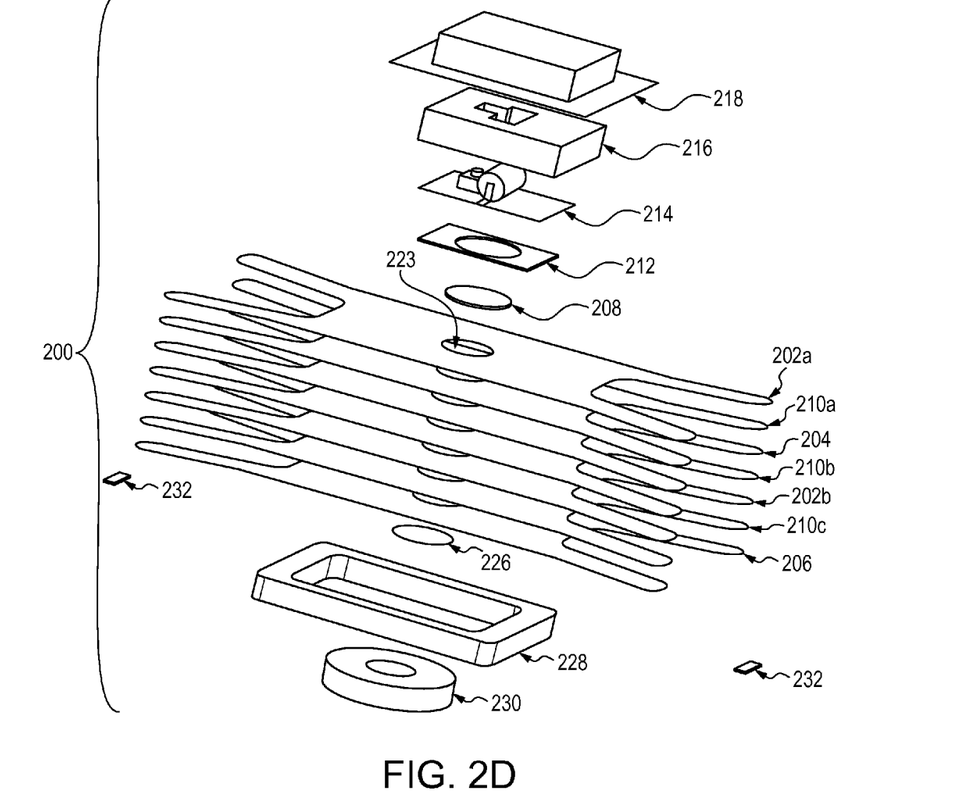
FIG. 2D is an at least partially exploded view of an alternative embodiment of the subcutaneous access device illustrated in FIG. 2C.

Interposed between the first and second securement layers 202a, 202b, and illustrated in FIG. 2B and FIG. 2D, is a layer of reflective or absorbing film 204. As described with respect to FIG. 1, the reflective or absorbing film 204 comprises any suitable reflective or absorbing material having any suitable thickness. Preferably, thickness of the reflective or absorbing film 204 is such that it facilitates conformability with the body portion of interest with which it interfaces during use of the subcutaneous access device 200. In one embodiment, the reflective or absorbing film 204 has a thickness of about 50 microns or less. An exemplary reflective film 204 comprises a 25 -µm thick layer of aluminum foil.

Residing on a side of the second securement layer 202b opposite the reflective or absorbing film 204 is an optional conformable layer 206. When present, the conformable layer 206 generally imparts additional flexibility and strength to the subcutaneous access device 200. The conformable layer 206 comprises any suitable material having any suitable thickness. An exemplary conformable material comprises polyurethane. In one embodiment, the conformable layer 206 comprises a 150-µm thick polyurethane film.

The reflective or absorbing film 204 facilitates reflection of backscattered light through optically transparent layer 208 or absorption of such light at the interface. As described above with respect to FIG. 1, the optically transparent layer 208 comprises any suitable material having any suitable thickness. Materials useful for the optically transparent layer 208 include, for example, polyurethane, polyethylene, poly (meth)acrylate, polyester, polydimethylsiloxane, and hydrocolloid gels (also referred to as hydrogels) or other highly transmissive, conformable materials as known to those of ordinary skill in the art. In one embodiment, the optically transparent layer 208 comprises a hydrogel. Any suitable hydrogel can be used, preferably one that provides good optical coupling and thermal properties. An exemplary hydrogel material is available from entrotech, inc. (Columbus, Ohio) under the trade designation, entrotape 974.

The optically transparent layer 208 can be any suitable thickness. In an exemplary embodiment, the optically transparent layer 208 comprises a hydrogel layer having a thickness of about 500 microns to about 2,000 microns, preferably a thickness of about 800 microns to about 1,300 microns.

Between each of the first and second securement layers 202a, 202b and the reflective or absorbing film 204 are respective first and second adhesive layers 210a, 210b. The first and second adhesive layers 210a, 210b comprise any suitable material having any suitable thickness. Each of the first and second adhesive layers 210a, 210b may consist of a different adhesive material and/or a different thickness. In one embodiment, each of the first and second adhesive layers 210a, 210b comprises a 2-µm thick laminating adhesive.

Between the second securement layer 202b and the conformable layer 206 is a third adhesive layer 210c. The third adhesive layer 210c comprises any suitable material having any suitable thickness. The third adhesive layer 210c may be the same material and/or thickness as one or both of the first and second adhesive layers 210a, 210b in the subcutaneous access device 200. For example, the third adhesive layer 210c comprises a 2-µm thick laminating adhesive in the embodiment illustrated in FIG. 2B. Alternatively, the third adhesive layer 210c comprises a double-sided adhesive tape, such as that shown in the embodiment illustrated in FIG. 2D. An exemplary double-sided adhesive tape suitable for use as the third adhesive layer 210c is an approximately 50-µm thick double-sided, acrylic adhesive tape sold by entrotech, inc. (Columbus, Ohio) under the trade designation, entrotape 572.

Proximate and adhered to the optically transparent layer 208 with a fourth adhesive layer 212 is an electronics layer 214. Any suitable adhesive material having any suitable thickness can be used for the fourth adhesive layer 212. In one embodiment, the fourth adhesive layer 212 comprises a double-sided adhesive tape. Many suitable double-sided adhesive tapes are commercially available. For example, entrotech, inc. (Columbus, Ohio) provides a suitable double-sided adhesive tape under the trade designation, entrotape 572.

The electronics layer 214 comprises circuitry and related electronic components for electrical operation of the subcutaneous access device 200 in conjunction with the light source. Preferably, the electronics layer 214 comprises a flex circuit. When integral to the subcutaneous access device 200, the light source is preferably one of the components in the electronics layer 214. Other components contained within the electronics layer 214 are known to those of ordinary skill in the art and are selected accordingly. For example, such electronic components can include a power supply for the light source and related circuitry.

In one embodiment, the light source comprises a light-emitting diode (LED). According to an exemplary aspect of this embodiment, within electronics layer 214, the LED channel or channels for the LED light source are driven using a step-down switching regulator circuit. Any suitable regulator circuit can be used. For example, Linear Technology (Milpitas, Calif.) supplies a suitable "3.3V Input High Power Step-Down Switching Regulator Controller" under product code, LTC1649. The regulator circuit converts unregulated battery voltage to a lower regulated voltage and can be operated in two different modes, a constant current mode and a constant voltage mode. Mode of operation is determined by the feedback network used within the circuit. In an exemplary embodiment, output from the regulator circuit is connected directly to current limit resistors in series with each LED channel.

In one embodiment, multiple LED channels for the LED light source are operated in parallel. In its primary mode, the constant voltage mode, the parallel LED channels are driven by a fixed preset voltage. In the constant voltage mode, current within the parallel LED channels is determined by series resistance of each of the LED channels.

According to a further embodiment, regulated output voltage from operation of the regulator circuit in its primary mode is pulsed at a fixed frequency to provide at least one of reduced power consumption of the device and reduced heat production of the device. When pulsed, any suitable frequency can be used as known to those of ordinary skill in the art. In an exemplary embodiment, the regulated output voltage is pulsed at a frequency of about 600 Hertz. To effectuate such pulsing, the electronics layer 214 comprises a pulse width modulation (PWM) circuit.

In constant current mode, the parallel LED channels are driven by a voltage set to an initial potential through a primary feedback network. During operation, however, voltage changes in order to maintain the preset current limit through the use of a second feedback network. This preset current limit is determined based on the desired current through each LED channel; and, current is regulated through each LED channel based on feedback from the LED channel. It is to be understood that the parallel LED channels could be replaced with a single channel of LEDs in series.

According to further embodiments, the electronics layer 214 comprises other switching regulator architectures, low dropout regulator circuits, and/or PWM drive circuits. For example, when operating the regulator circuit in its primary mode with frequency pulsing, a PWM drive circuit controls the LED intensity. When the regulator circuit is operated in constant current mode, a PWM drive circuit can be used to control the current level.

Surrounding the electronics layer 214 is a foam pad 216, all of which is encapsulated under a protective film 218. The foam pad 216 comprises any suitable foam material in any suitable thickness for protection of the electronics layer 214. In an exemplary embodiment, the foam material comprises a carbon-filled cellular foam material. Suitable foam materials include those sold by Sekisui Voltek, LLC (Lawrence, Mass.) under the VOLARA trade designation (e.g., VOLARA Type A foam). In an exemplary embodiment, thickness of the foam pad 216 is about 5 mm to about 20 mm, preferably about 10 mm. It is to be understood, however, that a hard, durable material may be used in place of the foam material in order to provide at least semi-rigid protection for the electronics layer 214 against, for example, impact and/or compression.

The protective film 218 also comprises any suitable material in any suitable thickness for protection of the electronics layer 214. In an exemplary embodiment, the protective film 218 comprises a 6-µm thick polyurethane film. Such a protective film 218 can be formed using any suitable method. In one embodiment, the protective film 218 is vacuum-formed to encapsulate the underlying components.

In the embodiment illustrated in FIG. 2A and FIG. 2B, on an opposite side of the subcutaneous access device 200 from the protective film 218 is a fifth adhesive layer 220 for secure attachment of the device 200 to a patient's body. Preferably, given that it contacts skin on the patient's body during use of the subcutaneous access device 200, the fifth adhesive layer 220 is biocompatible. In one embodiment, the fifth adhesive layer 220 comprises an approximately 50-100 µm thick acrylic adhesive. Until attachment to the patient's body during use, a release layer 222 may be provided on an outwardly exposed surface of the device 200 adjacent the fifth adhesive layer 220. Any suitable release material can be used for the release layer 222, including a 75-µm thick release material available from entrotech, inc. (Columbus, Ohio) under the trade designation, entrofilm 302.

Extending through the subcutaneous access device 200 is a central opening 223 for passing of light through the device 200 in order to illuminate a body's surface through the optically transparent layer 208. The central opening 223 has any suitable shape and dimensions for desired passage of light through the device 200. Shape and/or dimensions of the central opening 223 as it passes through each of the layers within the device 200 can be the same or different, preferably approximately the same. In one embodiment, the central opening 223 has a diameter no greater than about 80% of the width of the layer through which it passes. In an exemplary embodiment, diameter of the central opening 223 is about 25 mm throughout the device 200.

During use, the subcutaneous access device 200 is attached to a patient's body in a manner such that the body portion of interest is between a light source integral to the subcutaneous access device 200 (generally represented as portion 224 in FIG. 2A and FIG. 2C) and a corresponding light detector. The attachment portion of the subcutaneous access device 200 allows the body portion of interest to be outwardly exposed (i.e., the subcutaneous access device 200 does not cover the body portion of interest on a side of the patient's body opposite the light source). In this manner, subcutaneous structures can advantageously be accessed without, for example, having to insert a needle through the subcutaneous access device 200.

When the subcutaneous access device 200 is to be attached and detached multiple times from a patient's body or patients' bodies (e.g., for multiple uses), it may be desirable to utilize the device 200 without the fifth adhesive layer 220 shown in the embodiment of FIG. 2A and FIG. 2B. For example, such a multiple use subcutaneous access device is shown in the alternative embodiment of FIG. 2C and FIG. 2D.

Within the subcutaneous access device 200 of FIG. 2C and FIG. 2D, positioned where the fifth adhesive layer 220 is positioned in the embodiment illustrated in FIG. 2A and FIG. 2B, is a protective covering 226. That is, the protective covering 226 is positioned on an opposite side of the subcutaneous access device 200 from the protective film 218. The protective covering 226 is generally sized and shaped to cover the central opening 223. In an exemplary embodiment, the protective covering 226 is a disc-shaped layer of protective film. The protective covering 226 may be any suitable protective film material of any suitable thickness. Materials useful for the protective covering 226 include, for example, polyurethane, polyethylene, poly(meth)acrylate, polyester, polydimethylsiloxane, and hydrocolloid gels (also referred to as hydrogels) or other highly transmissive, conformable materials as known to those of ordinary skill in the art. In one embodiment, the protective covering 226 comprises polyurethane (e.g., an approximately 150-μm (6-mil) thick polyurethane film). For example, entrotech, inc. (Columbus, Ohio) provides such a suitable protective film material using the trade designation, entrofilm 843. The protective covering 226 can include a sub-layer or coating for adhering the protective covering 226 to adjacent conformable layer 206. For example, a coating of glue (e.g., an approximately 50-μm (2-mil) thick glue coating) can be provide such adherence.

In an exemplary embodiment, such as that illustrated in FIG. 2D, the subcutaneous access device 200 includes one or more light controlling features. For example, adjacent the protective covering 226 is a first foam boundary 228 as shown in FIG. 2D. The first foam boundary 228 comprises any suitable material having a suitable shape and dimensions to reduce leakage of light from the subcutaneous access device 200 during its use by absorbing or blocking light. In one embodiment, the first foam boundary 228 comprises a rectangular-shaped foam material. In an exemplary embodiment, the foam material comprises a carbon-filled cellular foam material. Suitable foam materials include those sold by Sekisui Voltek, LLC (Lawrence, Mass.) under the VOLARA trade designation (e.g., VOLARA Type A foam). In an exemplary embodiment, thickness of the first foam boundary 228 is about 5 mm to about 20 mm, preferably about 10 mm.

For redundancy and further control of light, fitted within the first foam boundary 228 is a second foam boundary 230. The second foam boundary 230 comprises any suitable material having a suitable shape and dimensions to reduce leakage of light from the subcutaneous access device 200 during its use by absorbing or blocking light. In one embodiment, the second foam boundary 230 comprises a disc-shaped foam material. In an exemplary embodiment, the foam material comprises a carbon-filled cellular foam material. Suitable foam materials include those sold by Sekisui Voltek, LLC (Lawrence, Mass.) under the VOLARA trade designation (e.g., VOLARA Type A foam). In an exemplary embodiment, thickness of the second foam boundary 230 is about 5 mm to about 20 mm, preferably about 10 mm. Most preferably, thicknesses of the first and second foam boundaries 228, 230 are approximately equal.

Also positioned to control light within the subcutaneous access device 200 illustrated in FIG. 2D are two tape tabs 232. The tape tabs 232 are positioned around outwardly exposed edges of the multi-layered structure within the device 200. Generally, such tape tabs 232 are opaque to light emitted from the light source during use of the subcutaneous access device 200. In a further embodiment, such tape tabs 232 are also reflective or absorbing of light emitted from the light source during use of the device 200. The tape tabs 232 used within a device 200 may each be the same material and/or dimensions, or each tape tab 232 may comprise different material and/or dimensions. In one embodiment, the tape tabs 232 each comprise a reflective material (e.g., aluminum foil or a similar metallic film) or absorbing material (e.g., a carbon substrate or other suitable substrate material made from, coated with, and/or impregnated with a light absorbing dye) laminated to a supporting structure, such as a laminate of the following layers: first securement layer 202a, first adhesive layer 210a, reflective or absorbing film 204, second adhesive layer 210b, and second securement layer 202b for further absorbing scattered light or redirecting light in relation to the body portion of interest under examination. When the outwardly exposed edges of the multi-layered structure within the device 200 are configured as such, enhanced illumination of subcutaneous structures is facilitated.

Figure 3:
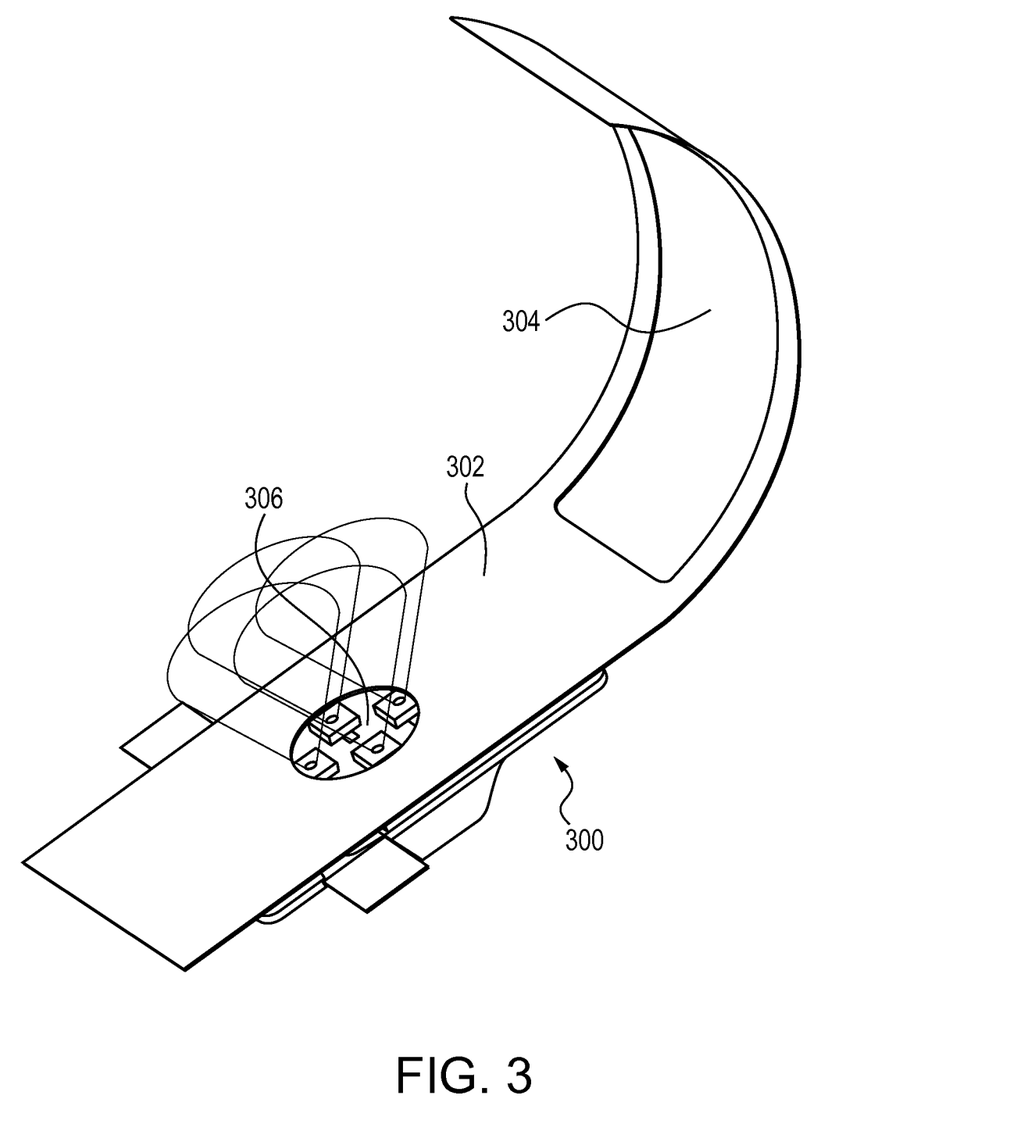
FIG. 3 is a perspective view of another exemplary subcutaneous access device of the present invention, as viewed from a side from which light is transmitted.

FIG. 3 illustrates an alternate embodiment of a subcutaneous access device 300 of the invention. In this embodiment, securement layer 302 comprises an opening 304 (e.g., a rectangular opening) for accessing a subcutaneous structure illuminated by a light source 306 therein without having to traverse the subcutaneous access device 300 itself when attached to a patient's body.

Figure 4:
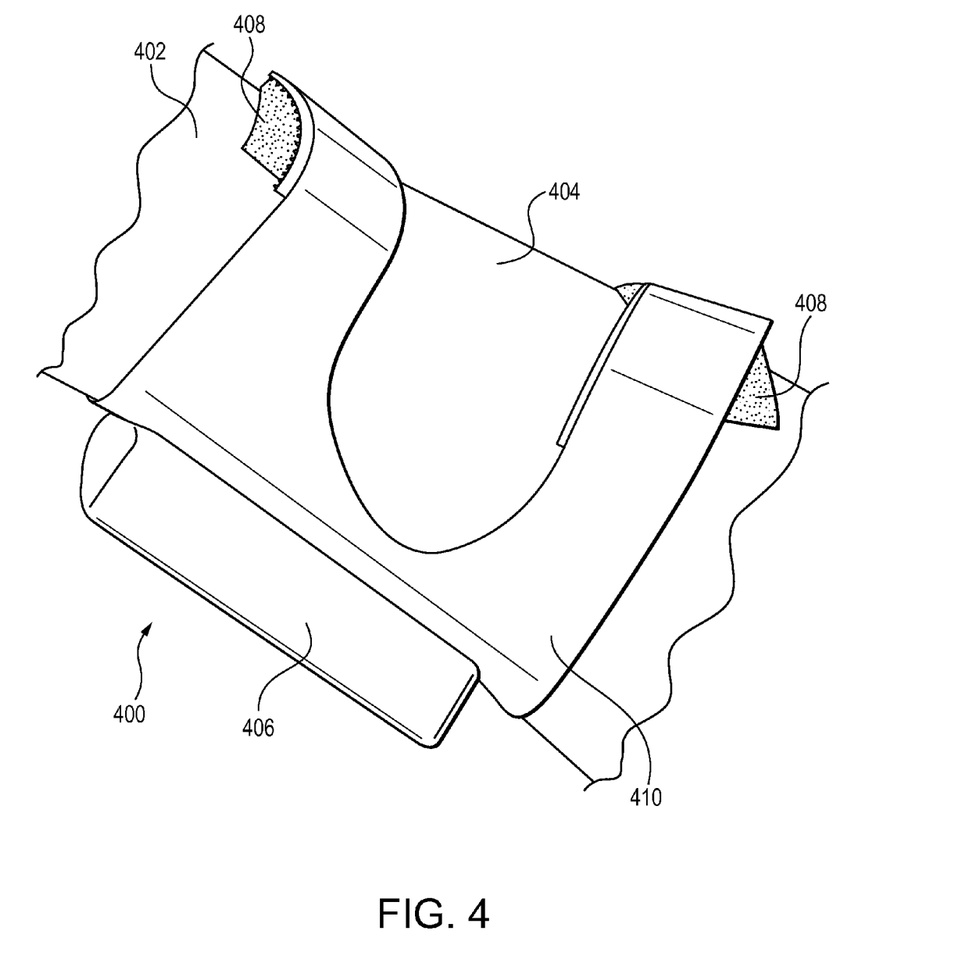
FIG. 4 is a perspective view of an exemplary subcutaneous access device of the present invention attached to a patient's forearm.

FIG. 4 illustrates a subcutaneous access device 400 attached to a patient's body 402 according to uses of the invention. As illustrated therein, the body portion of interest 404 is between a light source integral to the subcutaneous access device 400 (generally represented as portion 406 in FIG. 4) and a corresponding light detector (not shown). The attachment portion of the subcutaneous access device 400 allows the body portion of interest 404 to be outwardly exposed (i.e., the subcutaneous access device 400 does not cover the body portion of interest 404 on a side of the patient's body 402 opposite the portion 406 of the device 400 comprising the light source). In this embodiment, the attachment portion comprises matable hook-and-loop fasteners (a loop portion of which is partially illustrated as 408 in FIG. 4) on opposite ends of a securement layer 410.

Figure 5:
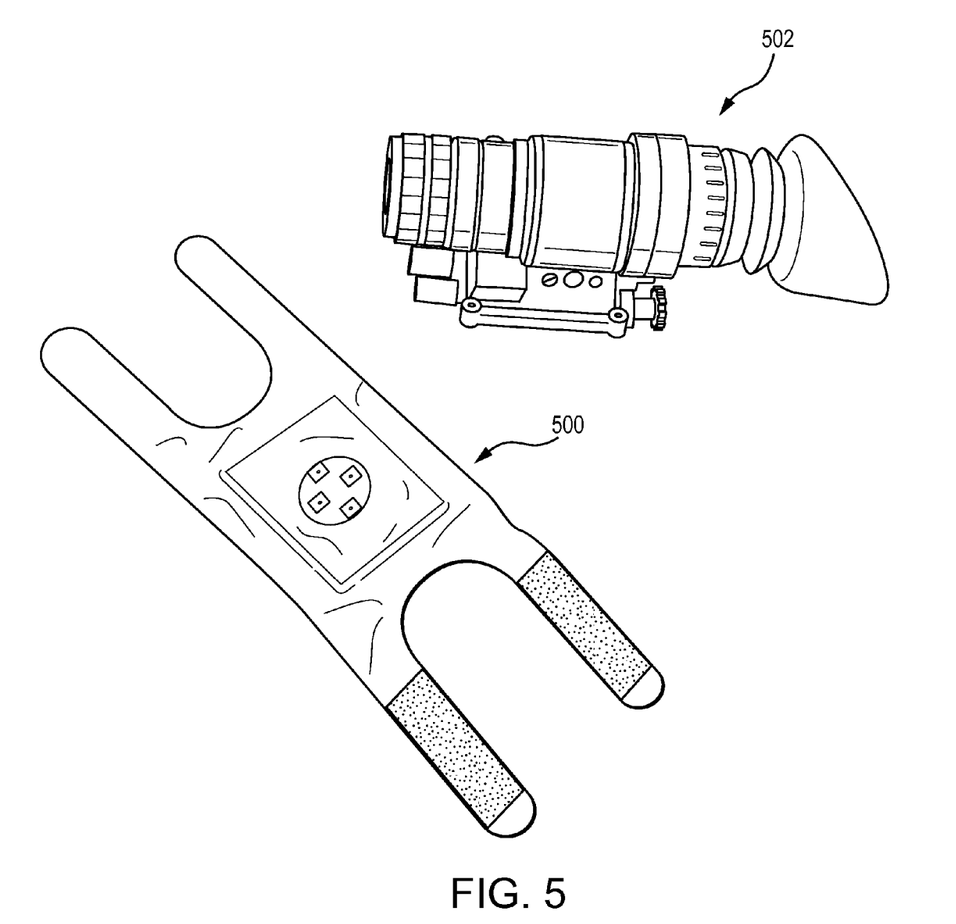
FIG. 5 is a perspective view of a kit of the invention comprising an exemplary subcutaneous access device and an exemplary light detector.

During use of a kit comprising the subcutaneous access device, light from the light source integral to the subcutaneous access device is detected using a corresponding light detector, preferably a low-level light detector. A variety of low-level light detectors are known, including image intensifier tubes, photomultiplier tubes, photodiodes, and charge coupled devices. In one embodiment of a kit of the invention, as illustrated in FIG. 5, a subcutaneous access device 500 is utilized in conjunction with night vision goggles 502 (generally, a form of image intensifier tube) used by a healthcare provider attempting to access a subcutaneous structure transilluminated thereby. This facilitates hands-free transillumination of a patient's body (e.g., a forearm) and, thus, easier intravenous access.

According to a further embodiment, a filter is attached to the lens on the night vision goggles 502 as known to those of ordinary skill in the art for enhanced resolution in moderate light conditions. Preferably, such a filter is adapted for partial light filtering (e.g., to remove interference from fluorescent light bulbs. An exemplary filter is a bandpass filter, many of which are commercially available as known to those of ordinary skill in the art.

Once the body portion of interest is sufficiently illuminated, subcutaneous structures therein can be accessed as known to those of ordinary skill in the art. Preferably, the subcutaneous structure is accessed directly through a patient's skin without the need to first penetrate the subcutaneous access device or other materials. As such, needles used to access the subcutaneous structure in exemplary embodiments are not dulled or clogged by the additional material through which they must first pass. This leads to more efficient and comfortable access.

Figure 6:
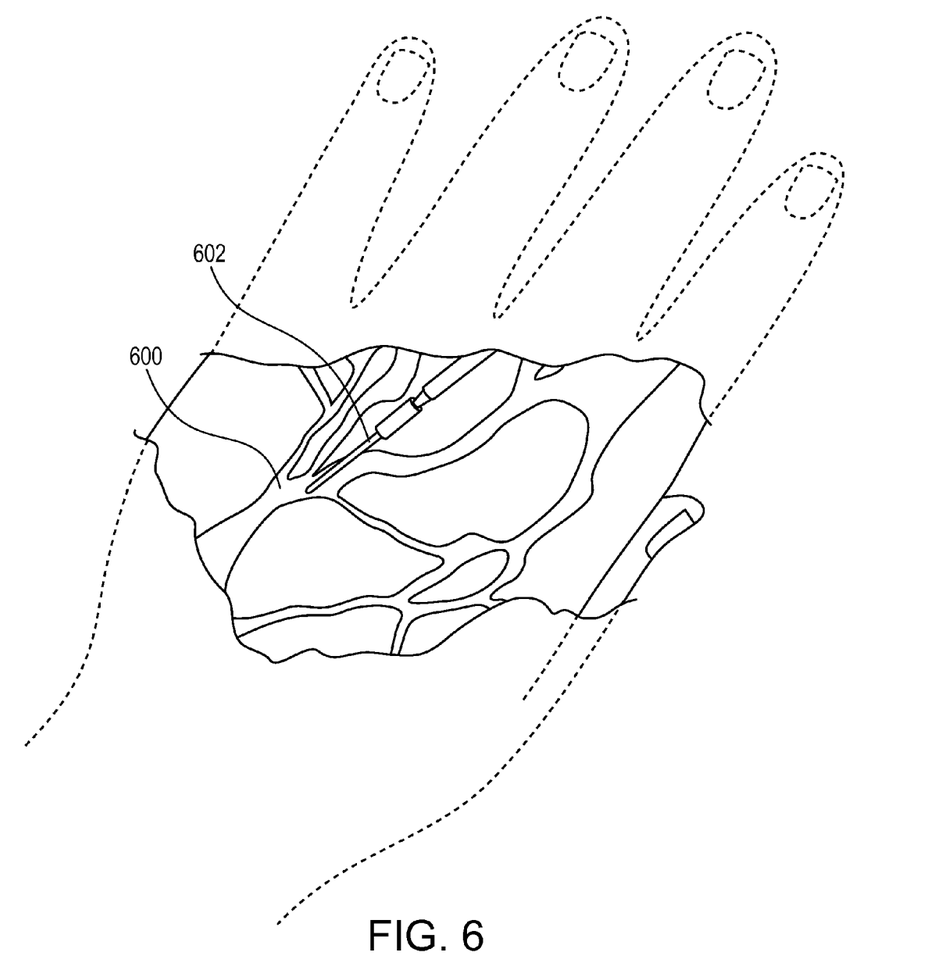
FIG. 6 is a black-and-white photograph of a transilluminated body portion of interest using a kit of the invention comprising a subcutaneous access device.

As evidenced by the photograph of FIG. 6, illumination of subcutaneous structures 600, such as the dorsal venous plexus of the hand and the ensuing cephalic and basilic veins shown in FIG. 6, when using subcutaneous access devices of the invention is beneficially enhanced. Enhanced visualization of subcutaneous structures facilitates easy and comfortable access to those structures. For example, a needle 602 can be rapidly and accurately guided into a patient's body to efficiently and painlessly access the desired subcutaneous structure. Therefore, the invention has widespread and desirable use in, for example, administering medical treatment to a patient.

Various modifications and alterations of the invention will become apparent to those skilled in the art without departing from the spirit and scope of the invention, which is defined by the accompanying claims. It should be noted that steps recited in any method or use claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

Further, as used throughout, ranges may be used as shorthand for describing each and every value that is within the range. Any value within the range can be selected as the terminus of the range. Similarly, any discrete value within the range can be selected as the minimum or maximum value recited in describing and claiming features of the invention.

The invention claimed is:

1. A subcutaneous access device comprising:
   a multi-layered structure capable of use in a medical imaging procedure;
   a light source for transillumination of a body portion of interest of a patient's body; and
   a non-adhesive attachment portion configured to attach the device to the patient's body in a manner such that the body portion of interest is outwardly exposed on a side of the patient's body opposite the light source,
   wherein the multi-layered structure comprises a conformable material comprising foam on a side of the device from which light is transmitted opposite the light source, such that the conformable material aids in prevention of light leakage from the light source.

2. The subcutaneous access device of claim 1, wherein the light source emits light having a wavelength of about 0.1 micron to about 1,500 microns.

3. The subcutaneous access device of claim 1, wherein the light source is coupled to a corresponding power source.

4. The subcutaneous access device of claim 3, wherein the light source comprises a portable power source.

5. The subcutaneous access device of claim 4, wherein the light source comprises a battery-powered light emitting diode or chemiluminescent source.

6. The subcutaneous access device of claim 1, wherein the device is configured for attachment to a patient's body in a manner such that the body portion of interest is between the light source and a corresponding light detector.

7. The subcutaneous access device of claim 1, wherein the attachment portion comprises at least one buckle.

8. The subcutaneous access device of claim 1, wherein the attachment portion comprises a hook-and-loop fastener.

9. The subcutaneous access device of claim 1, wherein outwardly exposed edges of the multi-layered structure comprise a reflective or absorbing material for redirecting of light in relation to the body portion of interest.

10. The subcutaneous access device of claim 1, wherein the device provides hands-free transillumination of the body portion of interest.

11. The subcutaneous access device of claim 1, wherein the device is disposable.

12. The subcutaneous access device of claim 1, wherein the device is capable of multiple effective uses.

13. A kit for subcutaneous access, comprising:
    the subcutaneous access device of claim 1; and
    a light detector for detecting light emitted from the subcutaneous access device.

14. The kit of claim 13, wherein the light detector comprises a low-level light detector.

15. The kit of claim 13, wherein the light detector comprises night vision goggles.

16. Use of the kit of claim 13 for access of a subcutaneous structure, comprising steps of:
    providing the kit of claim 13;
    utilizing the kit by positioning the subcutaneous access device on the patient's body such that the body portion of interest is outwardly exposed on a side of the patient's body opposite the light source; and,
    detecting light emitted from the subcutaneous access device using the light detector.

17. Use of the kit of claim 13 for access of a subcutaneous structure, comprising steps of:
    providing the kit of claim 13;
    utilizing the kit by positioning the subcutaneous access device on the patient's body such that the body portion of interest is outwardly exposed on a side of the patient's body opposite the light source; and,
    detecting light emitted from the subcutaneous access device using the light detector,
    wherein such use is proximate a battlefield.

18. Use of the kit of claim 13 for access of a subcutaneous structure, comprising steps of:
    providing the kit of claim 13;
    utilizing the kit by positioning the subcutaneous access device on the patient's body such that the body portion of interest is outwardly exposed on a side of the patient's body opposite the light source; and,
    detecting light emitted from the subcutaneous access device using the light detector,
    wherein such use is in a forward surgical unit of a temporary battlefield installation.

19. Use of the kit of claim 13 for access of a subcutaneous structure, comprising steps of:
provide the kit of claim 13;
utilizing the kit by positioning the subcutaneous access device on the patient's body such that the body portion of interest is outwardly exposed on a side of the patient's body opposite the light source; and,
detecting light emitted from the subcutaneous access device using the light detector,
wherein the subcutaneous access device is configured to be attached to the patient's body such that the body portion of interest is between the light source and the light detector.

20. Use of the kit of claim 13 for access of a subcutaneous structure, comprising steps of:
providing the kit of claim 13;
utilizing the kit by positioning the subcutaneous access device on the patient's body such that the body portion of interest is outwardly exposed on a side of the patient's body opposite the light source; and,
detecting light emitted from the subcutaneous access device using the light detector,
wherein the body portion of interest is transilluminated hands-free.

21. The subcutaneous access device of claim 1, wherein at least one layer of material capable of being securely attached at opposite ends thereof laterally extends from the subcutaneous access device.

22. The subcutaneous access device of claim 1, wherein the attachment portion of the device comprises an elastic sleeve or cuff having a sufficiently smaller diameter than a limb to which the device is to be applied.

23. The subcutaneous access device of claim 22, wherein the elastic sleeve or cuff is inflatable.

24. The subcutaneous access device of claim 1, wherein the device comprises a watch configuration.

25. The subcutaneous access device of claim 1, wherein outwardly exposed edges of the multi-layered structure comprise an absorbing material for redirecting of light in relation to the body portion of interest.

26. The subcutaneous access device of claim 1, wherein the attachment portion of the device comprises at least one of laces, strings, and bands.

27. The subcutaneous access device of claim 1, wherein the attachment portion of the device comprises a band.

28. The subcutaneous access device of claim 1, wherein the conformable material comprises a first foam boundary.

29. The subcutaneous access device of claim 28, wherein the conformable material comprises a second foam boundary fitted within the first foam boundary.

30. The subcutaneous access device of claim 1, further comprising tabs positioned around outwardly exposed edges of the multi-layered structure within the device, wherein the tabs are opaque to light emitted from the light source during use of the subcutaneous access device.

31. The subcutaneous access device of claim 1, wherein the non-adhesive attachment portion comprises an opening for accessing the subcutaneous structure illuminated by the light source without having to traverse the subcutaneous access device itself when the subcutaneous access device is attached to the patient's body.

* * * * *